United States Patent [19]

Reinert et al.

[11] Patent Number: 4,655,783
[45] Date of Patent: Apr. 7, 1987

[54] PROCESS FOR PHOTOCHEMICAL STABILIZATION OF NON-DYED AND DYED POLYAMIDE FIBRE MATERIAL AND MIXTURES THEREOF

[75] Inventors: Gerhard Reinert, Allschwil; Helmut Huber-Emden, Schönenbuch, both of Switzerland; Gerhard Back, Lörrach, Fed. Rep. of Germany

[73] Assignee: Ciba-Geigy Corporation, Ardsley, N.Y.

[21] Appl. No.: 797,098

[22] Filed: Nov. 12, 1985

[30] Foreign Application Priority Data

May 9, 1985 [CH] Switzerland .......................... 1975/85

[51] Int. Cl.$^4$ .......................... D06M 9/00; D06P 5/02; D06P 3/82
[52] U.S. Cl. .................................. 8/115.66; 8/115.64; 8/115.7; 8/442; 8/531; 8/602; 8/607; 8/608; 8/924; 8/926
[58] Field of Search .................. 8/602, 608, 442, 531, 8/607, 115.64, 115.66

[56] References Cited

U.S. PATENT DOCUMENTS

| | | | |
|---|---|---|---|
| 3,203,752 | 8/1965 | Mills et al. | 8/551 |
| 3,361,710 | 1/1968 | Sparks | 524/204 |
| 3,363,969 | 1/1968 | Brooks | 8/493 |
| 3,928,328 | 12/1975 | Dhaliwal | 546/7 |
| 4,383,835 | 5/1983 | Preuss et al. | 8/602 |
| 4,544,372 | 10/1985 | Heise et al. | 8/602 |

FOREIGN PATENT DOCUMENTS

| | | |
|---|---|---|
| 162811 | 10/1985 | European Pat. Off. . |
| 2625386 | 12/1977 | Fed. Rep. of Germany . |
| 799742 | 8/1958 | United Kingdom . |
| 1321645 | 6/1973 | United Kingdom . |
| 1392953 | 5/1975 | United Kingdom . |
| 2146357 | 4/1985 | United Kingdom . |

Primary Examiner—A. Lionel Clingman
Attorney, Agent, or Firm—Edward McC. Roberts; Meredith C. Findlay; Kevin T. Mansfield

[57] ABSTRACT

A process for photochemical stabilization of non-dyed and dyed polyamide fibre material and mixtures thereof with other fibres which comprises treating the fibre material with a fibre-reactive copper complex of bisazomethines prepared from, for example, salicylaldehydes and aliphatic diamines is described. Some of these copper complexes used are novel compounds. The polyamide fibre material, for example textile material, thus treated largely retains its extensibility and elasticity even after relatively prolonged exposure to light. In addition, a clear improvement in light-fastness is achieved in dyed material by treatment with the metal complex.

8 Claims, No Drawings

PROCESS FOR PHOTOCHEMICAL STABILIZATION OF NON-DYED AND DYED POLYAMIDE FIBRE MATERIAL AND MIXTURES THEREOF

The present invention relates to a process for photochemical stabilisation of non-dyed and dyed polyamide fibre material and mixtures thereof with other fibres by treating this material with water-insoluble copper complexes of bisazomethines prepared, for example, from substituted or unsubstituted salicylaldehydes and aliphatic diamines.

The use of copper salts, for example copper sulfate, for improving the light-fastness of dyeings on polyamide fibres with metal complex dyes is generally known; reference is made to the article by I. B. HANES in ADR 3 (1980), pages 19 and 20. However, inorganic or also organic copper salts frequently have the disadvantage that their absorption onto the polyamide fibres is only inadequate and non-uniform and they therefore have to be used in high concentrations in order to achieve the desired effect. Normally they can only be used for aftertreatment and in discontinuous processes.

European Patent Application No. 51,188 recommends treatment of the polyamide material with copper complexes of bisazomethines, prepared, for example, from substituted or unsubstituted salicylaldehydes and aromatic diamines, before, during or after dyeing to improve the light-fastness of polyamide dyeings.

Such agents for improving light-fastness have, however, an undesirable intrinsic colour and do not have a sufficiently adequate stability towards hydrolysis or acids, as is appropriately stated in European Patent Application No. 113,856 from the same Applicant.

It has now been found that, surprisingly, copper complexes of bisazomethines which are derived, for example, from substituted or unsubstituted salicylaldehydes and aliphatic diamines do not have the abovementioned disadvantages. In the concentrations used, these complexes have no undesirable intrinsic colour, and they also have a better stability towards acids and hydrolysis, than the most closely comparable complexes according to European Patent Application No. 51,188. In addition, they stain the fibre material less than the most closely comparable complexes.

The present invention thus relates to a process for photochemical stabilisation of non-dyed and dyed polyamide fibre material, or mixtures thereof with other fibres, which comprises treating the polyamide fibre material with a fibre-reactive, organic copper complex compound of the formula

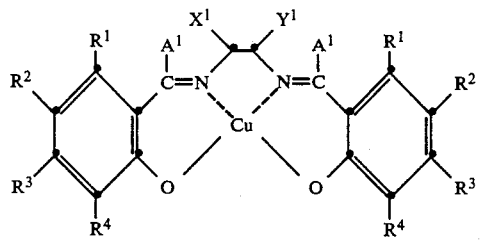

(1)

in which $A^1$ is hydrogen or $C_1$-$C_3$-alkyl, $R^1$, $R^2$, $R^3$ and $R^4$ independently of one another are each hydrogen, halogen, hydroxyl, hydroxyalkyl, alkyl, alkoxy, alkoxyalkoxy, alkoxy-alkoxyalkoxy, carboxymethoxy, alkylamino, dialkylamino, —$SO_2$—$NH_2$, —$SO_2NHR$ or —$SO_2NR^2$, in which R is alkyl or alkoxyalkyl and alkyl or alkoxy is in each case to be understood as a group with 1-4 C atoms, or $R^1$ and $R^2$ or $R^2$ and $R^3$ or $R^3$ and $R^4$, together with the C atoms to which they are bonded, form a fused-on benzene radical, and $X^1$ and $Y^1$ independently of one another are each hydrogen, $C_1$-$C_4$-alkyl or an aromatic radical, or $X^1$ and $Y^1$, together with the C atoms to which they are bonded, form a cycloaliphatic radical with 5-7 C atoms.

The present invention furthermore relates to the polyamide fibre material, or mixtures thereof with other fibres, stabilised photochemically by the present process, and the compounds of the formula (1) where these are novel per se.

The copper complex compounds of the formula (1) are in general water-insoluble if they contain no carboxymethoxy radicals (—O—$CH_2$—COOH) or salts thereof.

$A^1$ is preferably n-propyl, ethyl or especially methyl or in particular hydrogen. In the radicals $R^1$-$R^4$, halogen is fluorine, bromine or, in particular, chlorine. Examples of suitable alkyl radicals are methyl, ethyl, n-propyl, isopropyl and tert.-butyl, hydroxyalkyl radicals are, for example, hydroxyethyl, and examples of alkoxy radicals are methoxy, ethoxy and butoxy. An example of an alkoxyalkoxy radical is methoxyethoxy (also called 2-oxabutoxy) (O—$CH_2$—$CH_2$—O—$CH_3$), an example of an alkoxyalkoxyalkoxy radical is ethoxyethoxyethoxy (also called 3,6-dioxaoctyloxy) (—O—$CH_2$—$CH_2$—O—$CH_2$—$CH_2$—O—$CH_2$—$CH_3$) and an example of a dialkylamino radical is diethylamino. Particularly suitable sulfonamide radicals are the sulfonamide, N-methylsulfonamide and N,N-dimethylsulfonamide radical.

Two adjacent radicals $R^1$-$R^4$, together with the C atoms to which they are bonded, can also form a fused-on benzene radical. Such bisazomethines are derived from 2-hydroxy-1-naphthaldehyde, 3-hydroxy-2-naphthaldehyde or 1-hydroxy-2-naphthaldehyde.

The radicals X and Y can independently of one another be $C_1$-$C_4$-alkyl, for example methyl, ethyl, n-propyl, isopropyl, n-butyl, isobutyl, sec.-butyl and tert.-butyl. Aromatic radicals X and Y are, in particular, substituted or unsubstituted naphthyl and, especially, phenyl radicals. X and Y can also be linked to form a cycloaliphatic radical, for example cyclohexylene, cyclopentylene or cycloheptylene.

Preferably, $R^1$-$R^4$ independently of one another are each hydrogen, chlorine, bromine, methyl, ethyl, butyl, methoxy, ethoxy, methoxyethoxy, ethoxyethoxyethoxy or diethylamino or $R^1$ and $R^2$ together form a fused-on benzene radical.

Of the substituents $X^1$ and $Y^1$, preferably, one is hydrogen and the other is hydrogen, methyl, ethyl or phenyl, or $X^1$ and $Y^1$ together form a cyclohexylene radical.

Copper complexes which are preferably used are the water-insoluble copper complexes of the formula

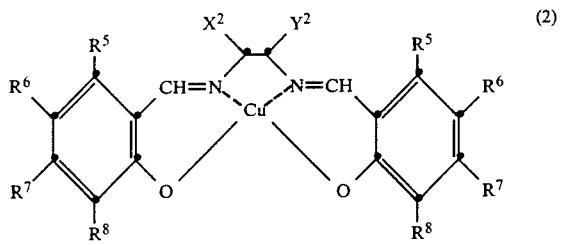

in which $R^5$–$R^8$ independently of one another are each hydrogen, hydroxyl, bromine, methyl, tert.-butyl, methoxy, methoxyethoxy, ethoxyethoxyethoxy or diethylamino, $X^2$ is hydrogen, methyl, ethyl or phenyl and $Y^2$ is hydrogen, or $R^5$ and $R^6$ together form a fused-on benzene radical, or $X^2$ and $Y^2$ together form a cyclohexylene radical.

Compounds which are of particular interest are those of the formula

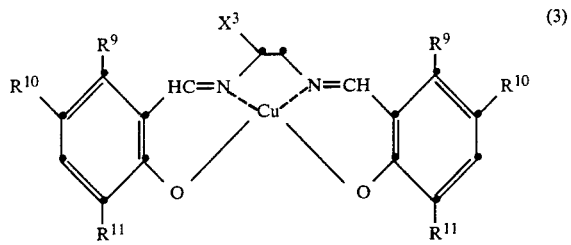

in which $R^9$, $R^{10}$ and $R^{11}$ independently of one another are each hydrogen, chlorine, bromine, methyl or methoxy, or in which $R^9$ and $R^{10}$ together form a fused-on benzene ring, and $X^3$ is hydrogen, methyl, ethyl or phenyl.

Compounds which are of chief interest, however, are those of the formula (3) in which $R^9$, $R^{10}$, $R^{11}$ and $X^3$ are hydrogen.

The compounds of the formula (1) are in some cases compounds which are known per se from, for example, Beilstein and Chemical Abstracts, and in some cases novel compounds. Thus, compounds of the formula (1) in which $R^3$ is methyl and $A^1$, $R^1$, $R^2$, $R^4$, $X$ and $X^2$ are hydrogen; $R^1$ and $R^4$ are methyl and $A^1$, $R^2$, $R^3$, $X^1$ and $Y^1$ are hydrogen; $R^2$ and $R^4$ are chlorine and $A^1$, $R^1$, $R^3$, $X^1$ and $Y^1$ are hydrogen; $R^4$ is methoxy and $A^1$, $R^4$, $R^2$, $R^3$, $X^1$ and $Y^1$ are hydrogen; $R^3$ is methoxy, methoxyethoxy, ethoxyethoxyethoxy or diethylamino and $A^1$, $R^1$, $R^2$, $R^4$, $X^1$ and $Y^1$ are hydrogen; $R^2$ is methoxyethoxy or ethoxyethoxyethoxy and $A^1$, $R^1$, $R^3$, $R^4$, $X^1$ and $Y^1$ are hydrogen; $R^2$ and $R^3$ are methoxyethoxy or ethoxyethoxyethoxy and $A^1$, $R^1$, $R^4$, $X^1$ and $Y^1$ are hydrogen, or one of the two substituents $R^3$ is hydroxyl and the other is methoxyethoxy or ethoxyethoxyethoxy and $A^1$, $R^1$, $R^2$, $R^4$, $X^1$ and $Y^1$ are hydrogen, are novel per se.

The compounds of the formula (1) are obtained in a manner which is known per se by reaction of 2 equivalents of the corresponding o-hydroxyaldehydes with 1 equivalent of the corresponding diamine to give the corresponding Schiff's base and subsequent metallisation with copper salts. However, it is also possible first to form the copper complex of the o-hydroxyaldehyde and then to react this with a corresponding diamine to give the copper complex of the bisazomethine of the formula (1).

It is also possible, without isolating the intermediates, to react the o-hydroxybenzaldehyde, the diamine and the copper salt in a single step in a so-called one-pot process directly to give the compound of the formula (1), or subsequently to modify, for example to alkylate, substituents, in particular hydroxyl groups, by a further reaction when the preparation of the compound of the formula (1) is complete. These 4 preparation methods are described by Pfeiffer in Liebigs Annalen der Chemie, Volume 503, pages 84–130 (1933).

The copper complexes of the formula (1) are advantageously applied from an aqueous bath, these advantageously being employed in an amount such that 5 to 200 μg, in particular 10 to 100 μg, of copper are present per g of polyamide fibre material.

The compounds of the formula (1) are advantageously employed as finely divided dispersions obtained by grinding in the presence of customary dispersants.

If the copper complexes are used for stabilising dyed material, the fibre material can be treated with the copper complex before, during or after dyeing. The copper complex is advantageously added directly to the dyeing or padding liquor. Dyeing is carried out continuously or batchwise. In the continuous procedure, the copper complexes can be fixed by steam or heat.

Polyamide material is understood as meaning synthetic polyamide, for example polyamide-6, polyamide-66 or polyamide-12. In addition to pure polyamide fibres, fibre mixtures of polyurethane and polyamide, thus, for example, tricot material of polyamide/polyurethane in a mixture ratio of 70:30, are also particularly suitable. In principle, the pure or mixed polyamide material can be in the most diverse processing forms, for example as fibres, yarn, woven fabric or knitted fabric.

In particular polyamide material which is exposed to light and heat and is in the form of, for example, automobile upholstery or carpets is especially suitable for treatment by the present process.

Dyeing is carried out in the customary manner, for example with metal complex dyes or with anthraquinone dyes or azo dyes. The known types of metal complex dyes are used, in particular the 1:2 chromium or 1:2 cobalt complexes of mono- or disazo- or -azomethine dyes, a large number of which are described in the literature. In addition to these, dyes from other classes of dyes are of course also suitable, for example disperse or vat dyes.

The following preparation instructions and examples serve to illustrate the invention. Parts and percentages are by weight. The percentage data relating to the additions to the individual treatment baths and dyebaths relate to the fibre material, unless indicated otherwise. Temperatures are in degrees Celsius.

PREPARATION INSTRUCTIONS FOR KNOWN COMPOUNDS

Instructions A:

3 g of ethylenediamine are added to a solution of 12.2 g of salicylaldehyde in 50 ml of ethanol. The mixture is stirred for a further 15 minutes and the precipitate which has separated out is filtered off with suction. 12.7 g (94% of theory) of yellow flakes of melting point 130°–131° of the formula

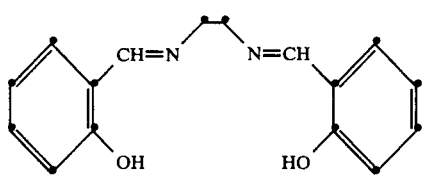

(101)

are obtained.

A solution, prepared with gentle warming, of 1.99 g of copper-II acetate monohydrate in 50 ml of dimethylformamide is added to 2.68 g of this compound, dissolved in 20 ml of dimethylformamide. The mixture is stirred for a further 15 minutes and the precipitate which has separated out is filtered off with suction and rinsed with a little dimethylformamide and ethanol. 2.8 g (86% of theory) of the compound of the formula

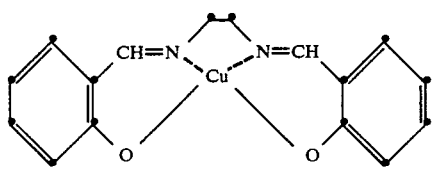

(102)

are obtained in the form of dark olive glossy crystals of melting point 324° (decomposition).

Instructions B:

0.6 g of ethylenediamine is added to a solution of 4.02 g of 5-bromo-2-hydroxybenzaldehyde in 20 ml of dimethylformamide, the bifunctional Schiff's base rapidly separating out as a yellow precipitate. A solution of 2 g of copper-II acetate monohydrate in 20 ml of dimethylformamide is then added, the mixture is stirred for a further 8 hours and the precipitate is filtered off with suction and washed with dimethylformamide and absolute ethanol. After drying, 4.69 g (96% of theory) of a grey-green solid substance of melting point 301°-302° (decomposition) and of the formula

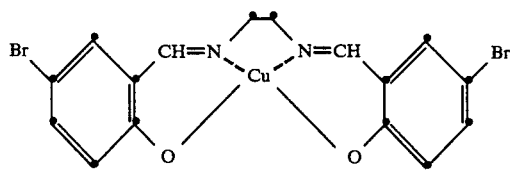

(103)

are obtained.

Instructions C–I:

The procedure described in Example 1 or 2 is repeated, but the aldehydes and diamines listed in the following Table I are used, affording the analogous copper complexes in similar yields.

TABLE I

| Instructions | Aldehyde | Diamine |
| --- | --- | --- |
| C | 5-chloro-2-hydroxy-benzaldehyde | ethylenediamine |
| D | 2-hydroxy-1-napth-aldehyde | ethylenediamine |
| E | 2-hydroxybenzaldehyde | 1-phenyl-ethylenediamine |
| F | 3-methyl-2-hydroxy-benzaldehyde | ethylenediamine |
| G | 5-methyl-2-hydroxy-benzaldehyde | ethylenediamine |
| H | 5-tert.-butyl-2-hydroxybenzaldehyde | ethylenediamine |

TABLE I-continued

| Instructions | Aldehyde | Diamine |
| --- | --- | --- |
| I | 2,4-dihydroxybenz-aldehyde | ethylenediamine |

Instructions J:

48.8 g of 2-hydroxybenzaldehyde, 12 g of ethylenediamine and then a solution, warmed to 85°, of 49.9 g of copper-II-sulfatepentahydrate in 200 ml of water are added in succession to 200 ml of 2 N sodium hydroxide solution at 85°, with stirring. The mixture is allowed to cool to room temperature (15°-25°), with stirring, and is filtered with suction and the residue on the filter is washed free from sulfate to give, after drying at 70° under reduced pressure (about 100 mm Hg), 62.5 g (94.8% of theory) of the compound of the formula (102) as a dark olive-coloured solid substance.

Instructions K–P:

The procedure described in Instructions B is repeated, but the aldehydes and diamines listed in the following Table II are used, affording the analogous copper complexes in similar yields:

TABLE II

| Instructions | Aldehyde | Diamine |
| --- | --- | --- |
| K | 5-chloro-2-hydroxy-benzaldehyde | ethylenediamine |
| L | 5-bromo-2-hydroxy-benzaldehyde | ethylenediamine |
| M | 2-hydroxy-1-naphthyl-aldehyde | ethylenediamine |
| N | 2-hydroxybenzaldehyde | methyl-ethylene-diamine |
| O | 2-hydroxybenzaldehyde | 1,2-cyclohexylene-diamine |
| P | 2-hydroxybenzaldehyde | 1-phenyl-ethylene-diamine |

Instructions Q

A warm solution of 3 g of copper-II acetate monohydrate in 50 ml of dimethylformamide is added at 60° C.. to a solution of 4.87 g of N,N'-bis[1-(2-hydroxyphenyl)-propylidene]ethylenediamine (prepared from 1 mole of ethylenediamine and 2 moles of 2-hydroxypropiophenone) in 50 ml of dimethylformamide. The mixture is allowed to cool and the precipitate is filtered off with suction and washed to give, after drying, 4.6 g (80% of theory) of the compound of the formula (1) in which $A^1$ is ethyl and $R^1$, $R^2$, $R^3$, $R^4$, $X^1$ and $Y^1$ are hydrogen as small violet-red needles (melting point 280°-281° C.).

PREPARATION EXAMPLES FOR NOVEL COMPOUNDS

EXAMPLE 1

4.2 g of N,N'-bis(6-hydroxy-2,5-dimethylbenzylidene)ethylenediamine (prepared from 1 mole of ethylenediamine and 2 moles of 3,6-dimethyl-2-hydroxy-benzaldehyde) are dissolved in 150 ml of ethanol and 50 ml of dimethylformamide under the influence of heat. A hot solution of 2.58 g of copper-II acetate monohydrate in 100 ml of ethanol is added, the mixture is allowed to cool, with stirring, and is filtered with suction to give, after drying, 4.72 g (91.4% of theory) of the compound of the formula (1) in which $R^1$ and $R^4$ are methyl and $A^1$, $R^2$, $R^3$, $X^1$ and $Y^1$ are hydrogen as pink violet-coloured platelets (melting point >340°).

EXAMPLE 2

The procedure described in Example 1 is repeated, but 4-methyl-2-hydroxy-benzaldehyde is employed as the starting component in the preparation of the Schiff's base, affording the compound of the formula (1) in which $R^3$ is methyl and $A^1$, $R^1$, $R^2$, $R^4$, $X^1$ and $Y^1$ are hydrogen as an olive-coloured solid substance in a similar yield.

EXAMPLE 3

The procedure described in Example 1 is repeated, but 4-methoxy-2-hydroxy-benzaldehyde is used as the starting component for the preparation of the Schiff's base, affording the compound of the formula (1) in which $R^3$ is methoxy and $A^1$, $R^1$, $R^2$, $R^4$, $X^1$ and $Y^1$ are hydrogen as olive-coloured platelets in a similar yield.

EXAMPLE 4

1.5 g of ethylenediamine are added to a suspension of 9.66 g of 4-diethylamino-2-hydroxybenzaldehyde in 20 ml of ethanol. The mixture is refluxed for 1 hour, allowed to cool and filtered with suction to give, after drying, 8.15 g (77% of theory) of the Schiff's base of the formula

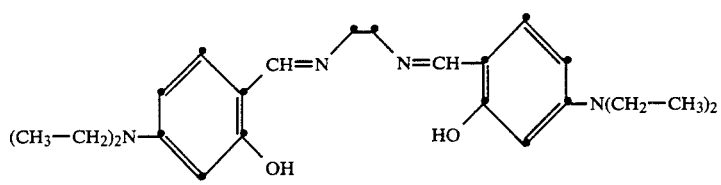

(104)

as a pale yellow substance which is novel per se (melting point: 137°–138°).

Hereafter, a solution of 3 g of copper-II acetate monohydrate in 100 ml of warm ethanol is added to a solution of 6.15 g of the Schiff's base of the formula (104) in 100 ml of warm ethanol. After stirring for 30 minutes, the mixture is filtered with suction. The residue on the filter is stirred with 30 ml of 1 N sodium hydroxide solution and 20 ml of ethanol for 30 minutes, filtered off with suction, washed neutral with water and dried. 6.9 g (93% of theory) of the compound of the formula (1) in which $R^3$ is diethylamino and $A^1$, $R^1$, $R^2$, $R^4$, $X^1$ and $Y^1$ are hydrogen are obtained as a dark grey finely crystalline substance (melting point 135°–136° (decomposition)). According to elemental analysis, the substance contains 1 mole of water of crystallisation.

EXAMPLE 5

The procedure described in Instructions B is repeated, but 3,5-dichloro-2-hydroxybenzaldehyde is used affording the compound of the formula (1) in which $R^2$ and $R^4$ are chlorine and $A^1$, $R^1$, $R^3$, $X^1$ and $Y^1$ are hydrogen as a violet pink-coloured solid substance in a similar yield.

EXAMPLE 6

The procedure described in Instructions B is repeated, but 3-methoxy-2-hydroxybenzaldehyde is used, affording the compound of the formula (1) in which $R^4$ is methoxy and $A^1$, $R^1$, $R^2$, $R^3$, $X^1$ and $Y^1$ are hydrogen as turquoise-coloured platelets in a similar yield.

EXAMPLE 7

5.32 g of 30% sodium hydroxide solution (diluted with 30 ml of ethanol) are added to a suspension of 7.24 g of the copper complex according to Instructions I in 300 ml of ethanol at 80°, with stirring. The mixture is allowed to cool and the precipitate is filtered off with suction and washed with ethanol. After drying, 7.4 g (77% of theory) of the corresponding sodium salt, which is novel per se, are obtained as a dark violet-coloured finely crystalline substance which, according to elemental analysis and acidimetric titration, contains 6 moles of water of crystallisation. Thereafter, 25.8 g of 2-methoxyethyltosylate are added to a suspension of 22.4 g of the disodium salt thus obtained in 300 ml of dimethylformamide. The mixture is stirred at 140° for 70 minutes. After cooling, it is poured into 1.5 liters of water, with stirring, and the precipitate is filtered off with suction and washed. The residue on the filter is stirred with 100 ml of 1 N sodium hydroxide solution for 1 hour, filtered off with suction, washed neutral and dried. 16.45 g (58% of theory) of the copper complex which, according to elemental analysis, contains 2 moles of water of crystallisation and corresponds to the formula (1) in which $R^3$ is methoxyethoxy and $A^1$, $R^1$, $R^2$, $R^4$, $X^1$ and $Y^1$ are hydrogen are obtained as pale turquoise-coloured substance (melting point 132°–135°).

EXAMPLE 8

The procedure described in Example 7 is repeated, but 2-[(2-ethoxy)-ethoxy]-ethyl tosylate is used, affording the compound of the formula (1) in which R is ethoxyethoxyethoxy and $A^1$, $R^1$, $R^2$, $R^4$, $X^1$ and $Y^1$ are hydrogen as a pale turquoise-coloured solid substance in a similar yield.

APPLICATION EXAMPLES

EXAMPLE 9

5 g of the condensation product of naphthalenesulfonic acid and formaldehyde, as a dispersant, dissolved in 7.5 ml of water, and 20 g of quartz beads (diameter about 1 mm) are added to 5 g of the compounds prepared according to Instructions A and the components are ground with a stirrer at about 1,600 revolutions per minute until the particle size is less than 2 μm. The dispersion is separated off from the quartz beads by means of a fine mesh sieve and adjusted to 20% of active substance with water.

Stirring in 0.3% of carboxymethylcellulose stabilises the dispersion.

Stable dispersions can be prepared from the compounds of Instructions B-Q and Examples 1-8 in the same manner.

EXAMPLE 10

Three pieces of a nylon 66 automobile cushion tricot weighing 15 g are treated in a dyeing apparatus with open treatment baths with liquors (liquor ratio of 1:25)

containing 2% of ammonium sulfate, 0.2% of the dye of the formula (in each case calculated on the fibre weight):

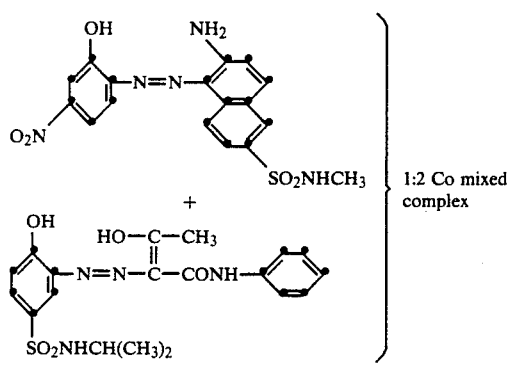

(105) 1:2 Co mixed complex and 0.35% of the wet-ground dispersion, obtained according to Example 9, of the compounds according to Instructions A or C. Dyeing without the addition of these compounds serves as a comparison. Treatment is initially carried out at 50° for 5 minutes, and the temperature is then increased to 95° at 2°/minute. The goods are treated at this temperature for 30 minutes and then cooled to 70°, rinsed cold, centrifuged and dried at 80° in a circulating air cabinet. The light-fastnesses of the dyeings are determined in accordance with SN-ISO 105-B02 (Xenon) and in accordance with DIN 75,202 (prov.) (Fakra). The dyeings (sample size about 18×10 cm) are furthermore exposed to heat over part of their area (about 18×4.5 cm) with covered side parts for 250 hours in accordance with DIN 75,202 (prov.). These samples are then tested for their tear strength and elongation in accordance with SNV 198,461.

The copper content of the fibre material dyed in the presence of the compound according to Instructions A or C was determined as 100 μg of Cu per g of fibre material.

The light-fastness of the dyeings which have been produced in the presence of the compounds according to Instructions A or C is clearly better than the light-fastness of the comparison dyeing without these compounds.

Furthermore, by adding the compounds according to Instructions A or C, the tear strength of the polyamide material after the exposure to light is considerably improved and the elongation is greater.

Similar results are achieved if 0.35% of the dispersion, obtained according to Example 9, of the compounds according to Instructions C or D-Q or Examples 1–8 is used.

EXAMPLE 11

2% dyeing with the red dye of the formula

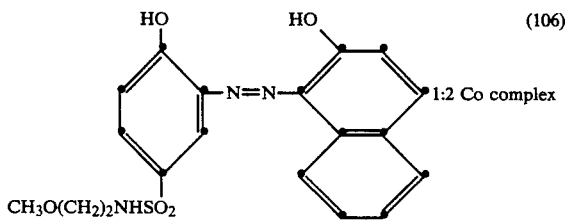

(106) 1:2 Co complex is carried out as described in Example 10, as well as in each case an analogous dyeing in which 0.35% of a dispersion, obtained according to the statements in Example 9, of the compounds according to Instructions A or C are additionally present. With this dyeing also, the addition of the Cu complexes according to Instructions A or C has the effect of a clear improvement in light-fastness, tear strength and elongation.

The copper content of the fibre material dyed in the presence of the compound according to Instructions A or C was 99 μg of Cu per g of fibre material.

EXAMPLE 12

Dyeing is carried out as described in Example 10 with 0.1% of the dye of the formula

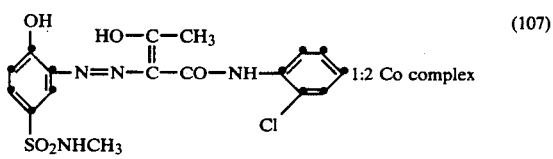

(107) 1:2 Co complex

The dyed material is investigated as described in Example 10.

With this dyeing also, the addition of the Cu complexes according to Instructions A or C has the effect of a clear improvement in the light-fastness, the tear strength and the elongation.

EXAMPLE 13

The compounds of Instructions A, B or C or Example 6 formulated according to Example 9 are tested on a nylon-66 filament yarn (7×3 tex). For this, beige dyeings are produced, these being obtained as described below.

Five yarn strands of 10 g of the nylon filament yarn are treated on a dyeing apparatus in open dyebaths with a liquor ratio of 1:40. The dyebaths are charged with 2 g/l of ammonium sulfate (pH 6.8), in each case 0 or 0.3% of the formulations, prepared according to Example 10, of the compounds according to Instructions A, B or C or Example 6 and the dye combination (dissolved in water).

0.04% dye 1   1:2 Co complex of the formula (yellow)   (107)

0.025% dye 2

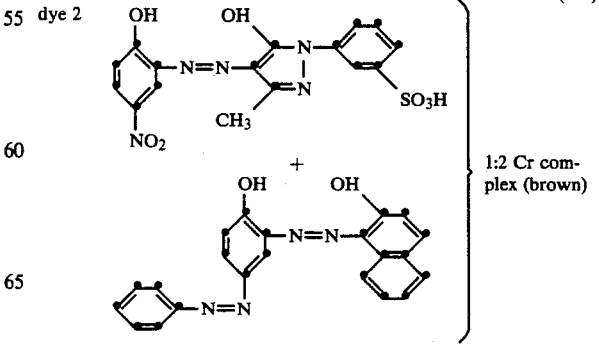

(108) 1:2 Cr complex (brown)

0.003% dye 3

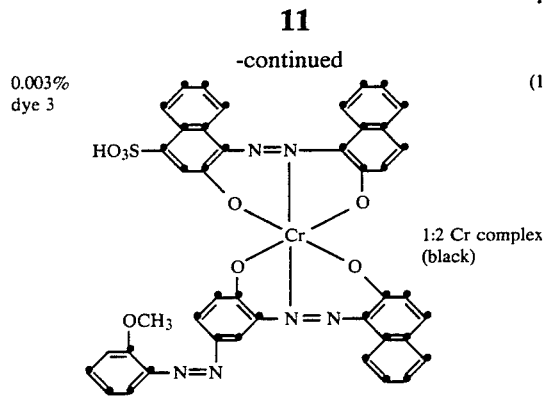

(109) 1:2 Cr complex (black)

Dyeing is started at 40° and the temperature is increased to 95° in the course of about 30 minutes. Dyeing is carried out at this temperature for 60 minutes and the dyed yarn is cooled to 70°, rinsed, centrifuged and dried.

On the one hand the light-fastness of the dyeings is determined in accordance with SN-ISO 105 B02 (Xenon) and DIN 75,202 (prov.) (Fakra), and on the other hand the yarn is wound onto cards (30 layers, gauge length about 22 cm) and exposed to heat for 200 hours in accordance with DIN 75,202 (prov.). Thereafter, the goods are tested for tear strength and elongation in accordance with SNV 97,461.

The addition of the compounds according to Instructions A, B or C or Example 6 also has the effect of a clear improvement in light-fastness, tear strength and elongation on the nylon filament yarn dyed with the above dyes. This also applies to the compounds according to Instructions D-Q or Examples 1–5, 7 or 8.

EXAMPLE 14

Four 10 g polyamide 66 filament yarn strands (7×3 tex) are prepared for treatment on a yarn-dyeing apparatus. 1% of 80% acetic acid (pH 5.5) is generally added to the treatment baths.

Bath No. 1 contains no further additive, bath No. 2 contains 0.35% of a formulation, obtained according to Example 9, of the compound according to Instructions A, bath No. 3 contains 0.2% of the dye of the formula

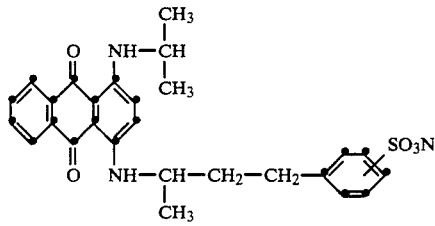

(110)

and bath No. 4 contains 0.2% of this dye and 0.35% of a formulation, obtained according to the information of Example 9, of the compound of Instructions A.

Treatment is carried out at a liquor ratio of 1:40 initially at 50°, the temperature is then increased to 95° in the course of 30 minutes and treatment is carried out for 60 minutes. Thereafter, the goods are cooled to 70°, rinsed cold, centrifuged and dried at 80°.

The treatments are tested as described in Example 13.

The addition of a copper compound according to Instructions A has the effect of a clear improvement in the tear strength and elongation in the samples treated in baths No. 2 and 4 in comparison with the samples treated without the copper compound. The light-fastness of the dyeing produced with bath 4 is also clearly improved in comparison with the dyeing produced with bath 3.

EXAMPLE 15

The procedure in Example 10 is repeated, but in each case 2 pieces of the nylon tricot weighing 10 g are dyed with a liquor, in a liquor ratio of 1:30, containing 2% of 80% acetic acid, 0 or 0.2% of the dispersion, obtained according to Example 9, of the compound according to Instructions A and 0.1% of the yellow dye of the formula

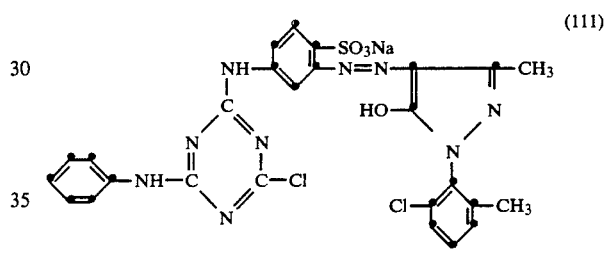

(111)

The addition of the compound according to Instructions A to the dye liquor has the effect of substantially improving the light-fastness of the dyeings and the tear strength and elongation of the polyamide material after exposure to light. This also applies if 1.0% of the dye of the formula (111) is used in the dye liquor. Similar results are also achieved if 0.09% of the orange-coloured dye of the formula

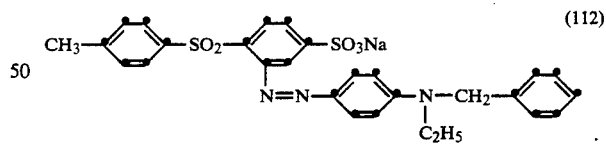

(112)

or 0.09% of the red dye of the formula

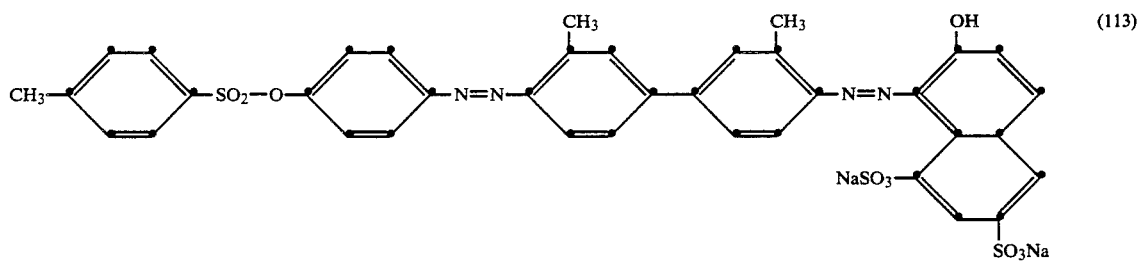

(113)

is used in the dye liquor. This also applies if 0.9% of the dye of the formula (112) or 0.9% of the dye of the formula (113) is used.

If 0.05% of the dye of the formula

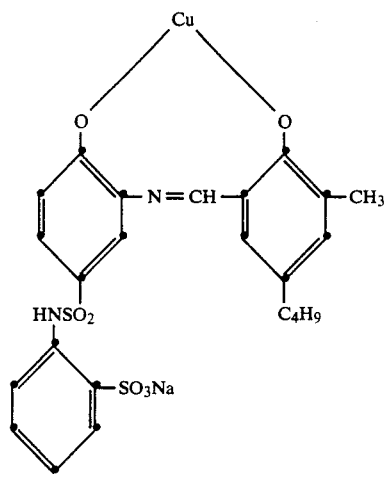

(114)

is used in addition to the copper complex compound according to Instructions A or C, even more clearly improved tear strength and elongation values are obtained on dyeing.

EXAMPLE 16

In each case 3 nylon-66 tricot pieces weighing 10 g are dyed with in each case 0.2% of the dyes of the formula (105), (106) or (107), rinsed and dried, as described in Example 10. Whilst series 1 of these dyeings remains unchanged, the two series 2 and 3 are padded, at a liquor pick-up of 75%, with a liquor containing ½g/l of a nonionic surfactant (adduct of 1 mole of nonylphenol and 9 ½ moles of ethylene oxide) and 2 g/l of the compound of the formula (102), formulated according to Example 9, and are dried at 120° for 1 minute. The dyeings of series 2 are heat-treated at 180° for 60 seconds, and those of series 3 are treated with saturated steam of about 100° for 5 minutes.

All the dyeings are tested as described in Example 10. It is found here that the dyeings of series 2 and 3 are significantly improved in respect of light-fastness when hot, tear strength and elongation in comparison with those of series 1.

What is claimed is:

1. A process for photochemical stabilisation of polyamide fibre material or a mixture thereof with another fibre material, which comprises treating the polyamide fibre material with a copper complex of the formula

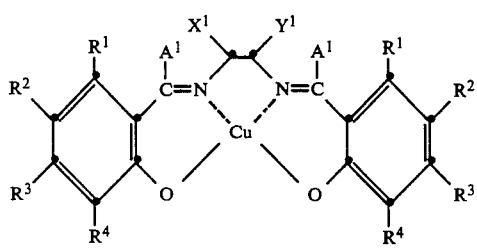

(1)

in which $A^1$ is hydrogen or $C^1$-$C^3$-alkyl, $R^1$, $R^2$, $R^3$ and $R^4$ are each hydrogen, halogen, hydroxyl, hydroxyalkyl, alkyl, alkoxy, alkyoxyalkoxy, alkoxyalkoxyalkoxy, carboxymethoxy, alkylamino, dialkylamino, $-SO_2NH_2$, $-SO_2NHR$ or $-SO_2NR^2$, in which R is alkyl or alkoxyalkyl and alkyl or alkoxy is in each case to be understood as a group with 1-4 C atoms, or $R^1$ and $R^2$ or $R^2$ and $R^3$ or $R^3$ and $R^4$, together with the C atoms to which they are bonded, form a benzene radical, and $X^1$ and $Y^1$ are each hydrogen, $C_1$-$C_4$-alkyl or an aromatic radical, or $X^1$ and $Y^1$, together with the C atoms to which they are bonded, form a cycloaliphatic radical with 5-7 C atoms.

2. The process according to claim 1, wherein a compound of the formula

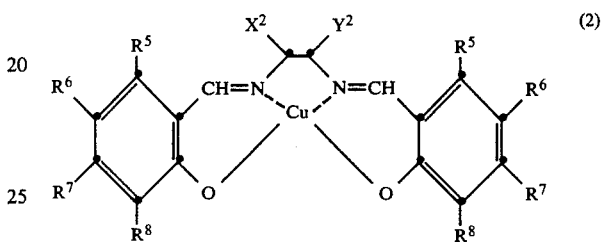

(2)

in which $R^5$, $R^6$, $R^7$ are each hydrogen, hydroxyl, chlorine, bromine, methyl, tert.-butyl, methoxy, methoxyethoxy, ethoxyethoxyethoxy or diethylamino, $X^2$ is hydrogen, methyl, ethyl or phenyl and $Y^2$ is hydrogen, or $R^5$ and $R^6$ together form a benzene radical, or $X^2$ and $Y^2$ together form a cyclohexylene radical, is used.

3. The process according to claim 2, wherein a compound of the formula (2) in which $R^5$, $R^6$, $R^7$ and $R^8$ are hydrogen and $X^2$ and $Y^2$ together form a cyclohexylene radical is used.

4. The process according to claim 1 wherein a compound of the formula

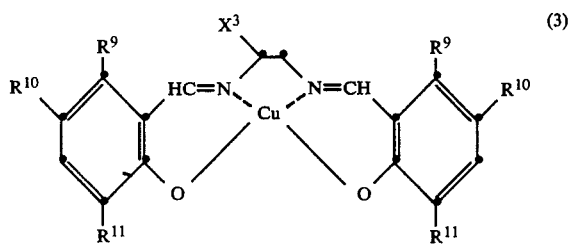

(3)

in which $R^9$, $R^{10}$ and $R^{11}$ are each hydrogen, chlorine, bromine methyl or methoxy, or $R^9$ and $R^{10}$ together form a benzene ring, and $X^3$ is hydrogen, methyl, ethyl or phenyl, is used.

5. The process according to claim 4, wherein a compound of the formula (3) in which $R^9$, $R^{10}$, $R^{11}$ and $X^3$ are hydrogen is used.

6. The process according to claim 1, wherein the copper complex is added directly to the dyebath.

7. The process according to claim 1, wherein the copper complex is employed in an amount such that 5 to 200 μg of copper are present per g of polyamide.

8. The process according to claim 1, wherein fibre mixtures of polyamide and polyurethane are used.

* * * * *